US011090481B2

(12) United States Patent
Smith et al.

(10) Patent No.: US 11,090,481 B2
(45) Date of Patent: Aug. 17, 2021

(54) WIRELESS POWER DELIVERY IN DYNAMIC ENVIRONMENTS

(71) Applicant: University of Washington through its Center for Commercialization, Seattle, WA (US)

(72) Inventors: Joshua R. Smith, Seattle, WA (US); Benjamin H. Waters, Kirkland, WA (US); Scott Wisdom, Seattle, WA (US); Alanson P. Sample, Hillsboro, OR (US)

(73) Assignee: University of Washington through its Center for Commercialization, Seattle, WA (US)

( * ) Notice: Subject to any disclaimer, the term of this patent is extended or adjusted under 35 U.S.C. 154(b) by 80 days.

(21) Appl. No.: 16/358,528

(22) Filed: Mar. 19, 2019

(65) Prior Publication Data

US 2019/0280527 A1 Sep. 12, 2019

Related U.S. Application Data

(63) Continuation of application No. 14/402,660, filed as application No. PCT/US2013/042085 on May 21, (Continued)

(51) Int. Cl.
*H02J 50/12* (2016.01)
*H02J 50/90* (2016.01)
(Continued)

(52) U.S. Cl.
CPC .......... *A61M 60/871* (2021.01); *A61M 60/50* (2021.01); *H02J 7/025* (2013.01);
(Continued)

(58) Field of Classification Search
CPC .... A61M 1/127; A61M 1/1086; A61M 1/101; A61M 2205/8243; A61M 1/122;
(Continued)

(56) References Cited

U.S. PATENT DOCUMENTS 3,553,736 A 1/1971 Kantrowitz et al.
4,809,681 A 3/1989 Kantrowitz et al.
(Continued)

FOREIGN PATENT DOCUMENTS

AU 2007349874 A2 6/2007
AU 2009246310 A1 11/2009
(Continued)

OTHER PUBLICATIONS

Akimoto, T., et al., "Rotary Blood Pump Flow Spontaneously Increases During Exercise Under Constant Pump Speed: Results of a Chronic Study," Artificial Organs 23(8):797-801, Aug. 1999.
(Continued)

*Primary Examiner* — Rexford N Barnie
*Assistant Examiner* — Thai H Tran
(74) *Attorney, Agent, or Firm* — Christensen O'Connor Johnson Kindness PLLC

(57) ABSTRACT

An adaptive system for efficient and long-range wireless power delivery using magnetically coupled resonators responds to changes in a dynamic environment, and maintains high efficiency over a narrow or fixed frequency range. The system uses adaptive impedance matching to maintain high efficiency. The wireless power transfer system includes a drive inductor coupled to a high-Q transmitter coil, and a load inductor coupled to a high-Q receiver coil. The transmitter coil and receiver coil for a magnetically coupled resonator. A first matching network is (i) operably coupled to the drive inductor and configured to selectively adjust the impedance between the drive inductor and the transmitter
(Continued)

coil, or (ii) is operably coupled to the load inductor and configured to selectively adjust the impedance between the load inductor and the receiver coil.

18 Claims, 7 Drawing Sheets

Related U.S. Application Data 2013, now abandoned, which is a continuation of application No. 13/843,884, filed on Mar. 15, 2013, now Pat. No. 8,827,889.

(60) Provisional application No. 61/734,236, filed on Dec. 6, 2012, provisional application No. 61/691,127, filed on Aug. 20, 2012, provisional application No. 61/649,496, filed on May 21, 2012.

(51) Int. Cl.

| | |
|---|---|
| *H02J 7/02* | (2016.01) |
| *A61M 60/871* | (2021.01) |
| *A61M 60/50* | (2021.01) |
| *H03H 7/40* | (2006.01) |
| *A61M 60/148* | (2021.01) |
| *A61M 60/205* | (2021.01) |

(52) U.S. Cl.
CPC .............. *H02J 50/12* (2016.02); *H02J 50/90* (2016.02); *A61M 60/148* (2021.01); *A61M 60/205* (2021.01); *A61M 2205/04* (2013.01); *A61M 2205/3515* (2013.01); *A61M 2205/3523* (2013.01); *A61M 2205/3561* (2013.01); *A61M 2205/8243* (2013.01); *H03H 7/40* (2013.01)

(58) Field of Classification Search
CPC ...... A61M 2205/04; A61M 2205/3515; A61M 2205/3523; A61M 2205/3561; H02J 50/90; H02J 50/12; H02J 7/025; H03H 7/40
USPC .......................................... 307/104; 320/108
See application file for complete search history.

(56) References Cited

U.S. PATENT DOCUMENTS

| | | | |
|---|---|---|---|
| 5,290,227 A | 3/1994 | Pasque | |
| 5,630,836 A | 5/1997 | Prem et al. | |
| 5,980,448 A | 11/1999 | Heilman et al. | |
| 6,331,744 B1 | 12/2001 | Chen et al. | |
| 6,445,956 B1 | 9/2002 | Laird et al. | |
| 6,669,624 B2 | 12/2003 | Frazier | |
| 6,764,373 B1 | 7/2004 | Osawa et al. | |
| 6,894,456 B2 | 5/2005 | Tsukamoto et al. | |
| 7,616,997 B2 | 11/2009 | Kieval et al. | |
| 7,741,734 B2 | 6/2010 | Joannopoulos et al. | |
| 7,825,543 B2 | 11/2010 | Karalis et al. | |
| D636,333 S | 4/2011 | Kulikowski | |
| 7,986,122 B2 | 7/2011 | Fornage et al. | |
| 8,022,576 B2 | 9/2011 | Joannopoulos et al. | |
| 8,035,255 B2 | 10/2011 | Kurs et al. | |
| 8,076,800 B2 | 12/2011 | Joannopoulos et al. | |
| 8,076,801 B2 | 12/2011 | Karalis et al. | |
| 8,084,889 B2 | 12/2011 | Joannopoulos et al. | |
| 8,097,983 B2 | 1/2012 | Karalis et al. | |
| 8,143,746 B2 | 3/2012 | Marzetta et al. | |
| 8,299,652 B2 | 10/2012 | Sample et al. | |
| 8,446,045 B2 | 5/2013 | Smith et al. | |
| 8,551,163 B2 | 10/2013 | Aber et al. | |
| 8,618,766 B2 | 12/2013 | Anderson et al. | |
| 8,767,871 B2 | 7/2014 | Park et al. | |
| 8,829,889 B2 | 9/2014 | Smith et al. | |
| 8,864,644 B2 | 10/2014 | Yomtov | |
| 9,415,149 B2 | 8/2016 | Smith et al. | |
| 2003/0032853 A1 | 2/2003 | Korakianitis et al. | |
| 2004/0116769 A1 | 6/2004 | Jassawalla et al. | |
| 2004/0172077 A1 | 9/2004 | Chinchoy et al. | |
| 2005/0085683 A1 | 4/2005 | Bolling et al. | |
| 2007/0035481 A1* | 2/2007 | Kim .................... G09G 3/296 345/68 |
| 2007/0060787 A1 | 3/2007 | Peters et al. | |
| 2008/0143192 A1 | 6/2008 | Sample et al. | |
| 2008/0183287 A1 | 7/2008 | Ayre | |
| 2008/0211320 A1* | 9/2008 | Cook .................... H02J 50/23 307/149 |
| 2008/0238528 A1* | 10/2008 | Wickersham ...... H03K 17/6877 327/432 |
| 2008/0278264 A1 | 11/2008 | Karalis et al. | |
| 2009/0046030 A1* | 2/2009 | Song ..................... H03J 3/06 343/852 |
| 2009/0134712 A1* | 5/2009 | Cook .................... H02J 50/12 307/104 |
| 2009/0267710 A1 | 10/2009 | Joannopoulos et al. | |
| 2010/0030304 A1 | 2/2010 | Haubrich et al. | |
| 2010/0045114 A1 | 2/2010 | Sample | |
| 2010/0052811 A1 | 3/2010 | Smith et al. | |
| 2010/0063347 A1 | 3/2010 | Yomtov et al. | |
| 2010/0081379 A1 | 4/2010 | Cooper et al. | |
| 2010/0096934 A1 | 4/2010 | Joannopoulos et al. | |
| 2010/0102639 A1 | 4/2010 | Joannopoulos et al. | |
| 2010/0102640 A1 | 4/2010 | Joannopoulos et al. | |
| 2010/0102641 A1 | 4/2010 | Joannopoulos et al. | |
| 2010/0117455 A1 | 5/2010 | Joannopoulos et al. | |
| 2010/0117456 A1 | 5/2010 | Karalis et al. | |
| 2010/0123353 A1 | 5/2010 | Joannopoulos et al. | |
| 2010/0123354 A1 | 5/2010 | Joannopoulos et al. | |
| 2010/0123355 A1 | 5/2010 | Joannopoulos et al. | |
| 2010/0127573 A1 | 5/2010 | Joannopoulos et al. | |
| 2010/0127574 A1 | 5/2010 | Joannopoulos et al. | |
| 2010/0127575 A1 | 5/2010 | Joannopoulos et al. | |
| 2010/0133918 A1 | 6/2010 | Joannopoulos et al. | |
| 2010/0133919 A1 | 6/2010 | Joannopoulos et al. | |
| 2010/0133920 A1 | 6/2010 | Joannopoulos et al. | |
| 2010/0141042 A1 | 6/2010 | Kesler et al. | |
| 2010/0148589 A1 | 6/2010 | Hamam et al. | |
| 2010/0164296 A1 | 7/2010 | Kurs et al. | |
| 2010/0164297 A1 | 7/2010 | Kurs et al. | |
| 2010/0164298 A1 | 7/2010 | Karalis et al. | |
| 2010/0171368 A1 | 7/2010 | Schatz et al. | |
| 2010/0171370 A1 | 7/2010 | Karalis et al. | |
| 2010/0181843 A1 | 7/2010 | Schatz et al. | |
| 2010/0181844 A1 | 7/2010 | Karalis et al. | |
| 2010/0181845 A1 | 7/2010 | Fiorello et al. | |
| 2010/0182216 A1 | 7/2010 | Schmidhammer | |
| 2010/0187911 A1 | 7/2010 | Joannopoulos et al. | |
| 2010/0187913 A1 | 7/2010 | Smith et al. | |
| 2010/0191036 A1 | 7/2010 | Sullivan | |
| 2010/0201203 A1 | 8/2010 | Schatz et al. | |
| 2010/0201205 A1 | 8/2010 | Karalis et al. | |
| 2010/0207458 A1 | 8/2010 | Joannopoulos et al. | |
| 2010/0219694 A1 | 9/2010 | Kurs et al. | |
| 2010/0225175 A1 | 9/2010 | Karalis et al. | |
| 2010/0231053 A1 | 9/2010 | Karalis et al. | |
| 2010/0231340 A1 | 9/2010 | Fiorello et al. | |
| 2010/0237706 A1 | 9/2010 | Karalis et al. | |
| 2010/0237707 A1 | 9/2010 | Karalis et al. | |
| 2010/0237708 A1 | 9/2010 | Karalis et al. | |
| 2010/0237709 A1 | 9/2010 | Hall et al. | |
| 2010/0253152 A1 | 10/2010 | Karalis et al. | |
| 2010/0259108 A1 | 10/2010 | Giler et al. | |
| 2010/0259110 A1 | 10/2010 | Kurs et al. | |
| 2010/0264745 A1 | 10/2010 | Karalis et al. | |
| 2010/0264747 A1 | 10/2010 | Hall et al. | |
| 2010/0277003 A1* | 11/2010 | Von Novak ............. H02J 50/90 307/104 |
| 2010/0277005 A1 | 11/2010 | Karalis et al. | |
| 2010/0277121 A1 | 11/2010 | Hall et al. | |
| 2010/0308939 A1 | 12/2010 | Kurs | |
| 2010/0327660 A1 | 12/2010 | Karalis et al. | |
| 2010/0327661 A1 | 12/2010 | Karalis et al. | |
| 2011/0012431 A1 | 1/2011 | Karalis et al. | |

(56) References Cited

U.S. PATENT DOCUMENTS

| | | |
|---|---|---|
| 2011/0018361 A1 | 1/2011 | Karalis et al. |
| 2011/0043046 A1 | 2/2011 | Joannopoulos et al. |
| 2011/0043047 A1 | 2/2011 | Karalis et al. |
| 2011/0043048 A1 | 2/2011 | Karalis et al. |
| 2011/0043049 A1 | 2/2011 | Karalis et al. |
| 2011/0049998 A1 | 3/2011 | Karalis et al. |
| 2011/0053500 A1* | 3/2011 | Menegoli ............ H02J 50/20 455/41.1 |
| 2011/0074218 A1 | 3/2011 | Karalis et al. |
| 2011/0074346 A1 | 3/2011 | Hall et al. |
| 2011/0074347 A1 | 3/2011 | Karalis et al. |
| 2011/0089895 A1 | 4/2011 | Karalis et al. |
| 2011/0095618 A1 | 4/2011 | Schatz et al. |
| 2011/0121920 A1 | 5/2011 | Kurs et al. |
| 2011/0140544 A1 | 6/2011 | Karalis et al. |
| 2011/0156493 A1 | 6/2011 | Bennett |
| 2011/0162895 A1 | 7/2011 | Karalis et al. |
| 2011/0169337 A1 | 7/2011 | Kozakai |
| 2011/0169339 A1 | 7/2011 | Karalis et al. |
| 2011/0193416 A1 | 8/2011 | Campanella et al. |
| 2011/0193419 A1 | 8/2011 | Karalis et al. |
| 2011/0198939 A1 | 8/2011 | Karalis et al. |
| 2011/0201870 A1 | 8/2011 | Forsell |
| 2011/0221278 A1 | 9/2011 | Karalis et al. |
| 2011/0241440 A1 | 10/2011 | Sakoda et al. |
| 2011/0304408 A1 | 12/2011 | McKinzie, III |
| 2012/0007690 A1 | 1/2012 | van Bezooijen |
| 2012/0049648 A1 | 3/2012 | Choi et al. |
| 2012/0080957 A1 | 4/2012 | Cooper et al. |
| 2012/0153738 A1 | 6/2012 | Karalis et al. |
| 2012/0161536 A1 | 6/2012 | Kamata et al. |
| 2012/0217926 A1 | 8/2012 | Yoon et al. |
| 2012/0235636 A1 | 9/2012 | Partovi |
| 2012/0243579 A1 | 9/2012 | Premakanthan et al. |
| 2012/0248888 A1 | 10/2012 | Kesler et al. |
| 2013/0278209 A1 | 10/2013 | Von Novak, III et al. |
| 2013/0310630 A1 | 11/2013 | Smith et al. |
| 2014/0015328 A1 | 1/2014 | Beaver et al. |
| 2014/0070623 A1 | 3/2014 | Keeling et al. |
| 2014/0073838 A1 | 3/2014 | Dague et al. |
| 2014/0275727 A1 | 9/2014 | Bonde et al. |
| 2015/0280444 A1 | 10/2015 | Smith et al. |
| 2018/0159529 A1* | 6/2018 | Reusch ............... G05F 1/571 |

FOREIGN PATENT DOCUMENTS

| | | |
|---|---|---|
| AU | 2010200044 A1 | 1/2010 |
| CA | 2 615 123 A1 | 1/2007 |
| CA | 2 682 284 A1 | 10/2008 |
| CA | 2 724 341 A1 | 11/2009 |
| CN | 101258658 A | 9/2008 |
| CN | 101682216 A | 3/2010 |
| CN | 101860089 A | 10/2010 |
| EP | 1 902 505 A2 | 3/2008 |
| EP | 2 130 287 A1 | 12/2009 |
| EP | 2 281 322 A1 | 2/2011 |
| EP | 2 306 615 A2 | 4/2011 |
| EP | 2 306 616 A2 | 4/2011 |
| EP | 2 340 611 A1 | 7/2011 |
| EP | 2 345 100 A1 | 7/2011 |
| JP | 2009-501510 A | 1/2009 |
| JP | 2011-177018 A | 9/2011 |
| JP | 2012-502602 A | 1/2012 |
| KR | 20080031398 A | 4/2008 |
| KR | 20100015954 A | 2/2010 |
| KR | 20110014649 A | 2/2011 |
| KR | 20110069182 A | 6/2011 |
| KR | 20110074761 A | 7/2011 |
| WO | 2007/008646 A2 | 1/2007 |
| WO | 2008/118178 A1 | 10/2008 |
| WO | 2009/140506 A1 | 11/2009 |
| WO | 2010/009399 A1 | 1/2010 |
| WO | 2010/036980 A1 | 4/2010 |
| WO | 2010/039967 A1 | 4/2010 |
| WO | 2010/108191 A1 | 9/2010 |
| WO | 2011/146661 A2 | 11/2011 |
| WO | 2013/177205 A1 | 11/2013 |
| WO | 2016/019159 A1 | 2/2016 |

OTHER PUBLICATIONS

Ali, A.N.A., et al., "A Survey of Maximum PPT Techniques of PV Systems," Proceedings of the IEEE Energytech Conference, Cleveland, Ohio, May 29-31, 2012, pp. 1-17.

Amir, O., et al., "Peripheral Vascular Reactivity in Patients With Pulsatile vs Axial Flow Left Ventricular Assist Device Support," Journal of Heart and Lung Transplantation 25(4):391-394, Apr. 2006.

Ayre, P.J., et al., "Sensorless Flow and Head Estimation in the VentrAssist Rotary Blood Pump," Artificial Organs 24(8):585-588, Aug. 2000.

Beh, T.C., et al., "Automated Impedance Matching System for Robust Wireless Power Transfer Via Magnetic Resonance Coupling," IEEE Transactions on Industrial Electronics 60(9):3689-3698, Jun. 2012.

Beh, T.C., et al., "Wireless Power Transfer System Via Magnetic Resonant Coupling at Fixed Resonance Frequency—Power Transfer System Based on Impedance Matching," World Electric Vehicle Journal 4:744-753, Nov. 2010.

Birks, E.J., et al., "Left Ventricular Assist Device and Drug Therapy for the Reversal of Heart Failure," New England Journal of Medicine 355(18):1873-1884, Nov. 2006.

Bishopric, N.H., "Evolution of the Heart From Bacteria to Man," Annals of the New York Academy of Sciences 1047:13-29, Jun. 2005.

Bonde, P., et al., "National Trends in Readmission (REA) Rates Following Left Ventricular Assist Device (LVAD) Therapy," Journal of Heart and Lung Transplantation 30(4 Suppl):S9, Apr. 2011.

Boston, J.R., et al., "Control Issues in Rotary Heart Assist Devices," Proceedings of the American Control Conference, Chicago, Jun. 28-30, 2000, pp. 3473-3477.

Choi, S., et al., "A Sensorless Approach to Control of a Turbodynamic Left Ventricular Assist System," IEEE Transactions on Control Systems Technology 9(3):473-482, May 2001.

Christ, A., et al., "The Virtual Family—Development of Surface-Based Anatomical Models of Two Adults and Two Children for Dosimetric Simulations," Physics in Medicine and Biology 55(2):N23-N38, Jan. 2010.

Cowger, J., et al., "The Development of Aortic Insufficiency in Left Ventricular Assist Device-Supported Patients," Circulation: Heart Failure 3(6):668-674, Nov. 2010.

Crow, S., et al., "Gastrointestinal Bleeding Rates in Recipients of Nonpulsatile and Pulsatile Left Ventricular Assist Devices," Journal of Thoracic and Cardiovascular Surgery 137(1):208-215, Jan. 2009.

Demirozu, Z.T., et al., "Arteriovenous Malformation and Gastrointestinal Bleeding in Patients With the HeartMate II Left Ventricular Assist Device," Journal of Heart and Lung Transplantation 30(8):849-853, Aug. 2011.

Deyle, T., and M. Reynolds, "PowerPACK: A Wireless Power Distribution System for Wearable Devices," Proceedings of the 12th IEEE International Symposium on Wearable Computers, Pittsburgh, Pa., Sep. 28-Oct. 1,2008, pp. 91-98.

Duong, T.P., and J.-W. Lee, "Experimental Results of High-Efficiency Resonant Coupling Wireless Power Transfer Using a Variable Coupling Method," IEEE Microwave and Wireless Components Letters 21(8):442-444, Aug. 2011.

Fletcher, N.H., and T.D. Rossing, "Coupled Vibrating Systems," Chap. 4, in "The Physics of Musical Instruments," 2d. ed., Springer-Verlag: New York, 1998, pp. 102-132.

Giridharan, G.A., and M. Skliar, "Physiological Control of Blood Pumps Using Intrinsic Pump Parameters: A Computer Simulation Study," Artificial Organs 30(4):301-307, Apr. 2006.

Goldstein, D.J., et al., "Driveline Infections in LVADs: Is It the Pump or the Patient?" Journal of Heart and Lung Transplantation 30(4 Suppl):S10, Apr. 2011.

(56) References Cited

OTHER PUBLICATIONS

Heidenreich, P.A., et al., "Forecasting the Impact of Heart Failure in the United States: A Policy Statement From the American Heart Association," Circulation: Heart Failure 6(3):606-619, May 2013.

Karantonis, D.M., et al., "Noninvasive Pulsatile Flow Estimation for an Implantable Rotary Blood Pump," Proceedings of the 29th Annual International Conference of the IEEE Engineering in Medicine and Biology Society (EMBS 2007), Lyon, France, Aug. 23-26, 2007, pp. 1018-1021.

Kiani, M., and M. Ghovanloo, "The Circuit Theory Behind Coupled-Mode Magnetic Resonance-Based Wireless Power Transmission," IEEE Transactions on Circuits and Systems I: Regular Papers 59(9):2065-2074, Sep. 2012.

Kiani, M., et al., "Design and Optimization of a 3-Coil Inductive Link for Efficient Wireless Power Transmission," IEEE Transactions on Biomedical Circuits and Systems 5(6):579-591, Dec. 2011.

Li, Y.Y., et al., "Downregulation of Matrix Metalloproteinases and Reduction in Collagen Damage in the Failing Human Heart After Support With Left Ventricular Assist Devices," Circulation 104(10):1147-1152, Sep. 2001.

Paing, T., et al., "Resistor Emulation Approach to Low-Power RF Energy Harvesting," IEEE Transactions on Power Electronics 23(3):1494-1501, May 2008.

Parnis, S.M., et al., "Progress in the Development of a Transcutaneously Powered Axial Flow Blood Pump Ventricular Assist System," ASAIO Journal 43(5):M576-M580, Sep.-Oct. 1997.

Pirbodaghi, T., et al., "Asymmetric Speed Modulation of a Rotary Blood Pump Affects Ventricular Unloading," European Journal of Cardio-Thoracic Surgery 43(2):383-388, Feb. 2013.

Pirbodaghi, T., et al., "Physiologic and Hematologic Concerns of Rotary Blood Pumps: What Needs to Be Improved?" Heart Failure Reviews 19(2):259-266, Mar. 2014.

PowerMat Technologies, "Powermat Wireless Charging System," Nov. 2011, <https://web.archive.org.web/20111115041555/http://www.powermat.com> [retrieved Mar. 2017], 1 page.

Pozar, D.M., "4.4: The Transmission (ABCD) Matrix," in "Microwave Engineering," 4th ed., John Wiley & Sons, Hoboken, N.J., 2012, pp. 188-194.

Ramrakhyani, A.K., et al., "Design and Optimization of Resonance-Based Efficient Wireless Power Delivery Systems for Biomedical Implants," IEEE Transactions on Biomedical Circuits and Systems 5(1):48-63, Feb. 2011.

Roger, V.L., et al., "Heart Disease and Stroke Statistics—2012 Update: A Report From the American Heart Association," Circulation 125(1):e2-e220, Jan. 2012.

Rose, E.A., et al., "Long-Term Use of a Left Ventricular Assist Device for End-Stage Heart Failure," New England Journal of Medicine 345(20):1435-1443, Nov. 2001.

Si, P., et al., "A Frequency Control Method for Regulating Wireless Power to Implantable Devices," IEEE Transactions on Biomedical Circuits and Systems 2(1):22-29, Mar. 2008.

Simon, D., et al., "Left Ventricular Assist Device-Related Infection: Treatment and Outcome," Clinical Infectious Diseases 40(8):1108-1115, Apr. 2005.

Sivaratnam, K., and J.M. Duggan, "Left Ventricular Assist Device Infections: Three Case Reports and a Review of the Literature," ASAIO Journal 48(1):2-7, Jan.-Feb. 2002.

Slaughter, M.S., et al., "Advanced Heart Failure Treated With Continuous-Flow Left Ventricular Assist Device," New England Journal of Medicine 361(23):2241-2251, Dec. 2009.

Stehlik, J., et al., "The Registry of the International Society for Heart and Lung Transplantation: Twenty-Seventh Official Adult Heart Transplant Report-2010," Journal of Heart and Lung Transplantation 29(10):1089-1103, Oct. 2010.

Thoratec Corporation, "HeartMate II® LVAS: Left Ventricular Assist System," Operating Manual, Document No. 103538, Rev. B, Nov. 2007, 157 pages.

Tsukiya, T., et al., "Use of Motor Current in Flow Rate Measurement for the Magnetically Suspended Centrifugal Blood Pump," Artificial Organs 21(5):396-401, May 1997.

Waters, T., et al., "Motor Feedback Physiological Control for a Continuous Flow Ventricular Assist Device," Artificial Organs 23(6):480-486, Jun. 1999.

Westaby, S., et al., "Circulatory Support With Attenuated Pulse Pressure Alters Human Aortic Wall Morphology," Journal of Thoracic and Cardiovascular Surgery 133(2):575-576, Feb. 2007.

Yeager, D.J., et al., "Chapter 14—WISP: A Passively Powered UHF RFID Tag With Sensing and Computation," in Ahson and Ilyas (eds.), "RFID Handbook: Applications, Technology, Security, and Privacy," CRC Press, Boca Raton, Florida, 2008, pp. 261-276.

Yoshizawa, M., et al., "Sensorless Estimation of Pressure Head and Flow of a Continuous Flow Artificial Heart Based on Input Power and Rotational Speed," ASAIO Journal 48(4):443-448, Jul.-Aug. 2002.

Allen, J.G., et al., "Quality of Life and Functional Status in Patients Surviving 12 Months After Left Ventricular Assist Device Implantation," Journal of Heart and Lung Transplanation 29(3)279-285, Mar. 2010.

Brown, W.C., "The History of Power Transmission by Radio Waves," IEEE Transactions on Microwave Theory and Techniques 32(9):1230-1242, Sep. 1984.

Cannon, B.L., et al., "Magnetic Resonant Coupling as a Potential Means for Wireless Power Transfer to Multiple Small Receivers," IEEE Transactions on Power Electronics 24(7):1819-1825, Jul. 2009.

Casanova, J.J., et al., "A Loosely Coupled Planar Wireless Power System for Multiple Receivers," IEEE Transactions on Individual Electronics 56(8):3060-3068, Aug. 2009.

Christ, A., et al., "Numerical Electromagnetic Analysis of Human Exposure for Wireless Power Transfer Systems," Proceedings of the Tenth International Congress of the European Bioelectromagnetics Association (EBEA), Rome, Feb. 21-24, 2011, 2 pages.

Baddour, L.M., et al., "Nonvalvular Cardiovascular Device-Related Infections," Circulation 108(16):2015-2031, Oct. 2003.

Christ, A., et al., "Evaluation of Wireless Resonant Power Transfer Systems With Human Electromagnetic Exposure Limits," IEEE Transactions on Electromagnetic Compatibility 55(2):265-274, Apr. 2013.

Economist, "Technology Monitor: A Wireless Heart," Apr. 12, 2011, <http://www.economist.com/node/21017837/print> [retrieved Jan. 22, 2015], 3 pages.

Ford, O., "Analysts See HeartWare Taking Lead in LVAD Market Position," Medical Device Daily Midday Report, Feb. 1, 2011, <http://www.medicaldevicedaily.com/servlet/com.accumedia.web.Dispatch . . . > [retrieved Jan. 22, 2015], 2 pages.

Hollister, S., "From Touchstone to Flashpoint: The Wireless Charging Standards War," The Verge, <http://www.theverge.com/2013/4/17/4236980/wireless-charging> [retrieved Jan. 26, 2015], 22 pages.

Holman, W.I., et al., "Infection in Permanent Circulatory Support: Experience From the REMATCH Trial," Journal of Hearth and Lung Transplantation 23(12):1359-1365, Dec. 2004.

Holman, W.L., et al., "Predictors of Death and Transplant in Patients With a Mechanical Circulatory Support Device: A Multi-institutional Study," Journal of Heart and Lung Transplantation 28(1):44-50, Jan. 2009.

Huang, G.T., "Intel Labs Seattle Shows Off New Sensing Interfaces, Self-Charging Robot, Wireless Power," Xconomy, Sep. 29, 2009, <http://www.xconomy.com/seattle/2009/09/29/intel-labs-seattle-shows-off . . . > [retrieved Jan. 26, 2015], 2 pages.

Moskowitz, A.J., et al., "The Cost of Long-Term LVAD Implantation," Annals of Thoracic Surgery 71(3, Suppl. 1):S195-S198, Mar. 2001.

Oz, M.C., et al., "Left Ventricular Assist Devices as Permanent Heart Failure Therapy: The Price of Progress," Annals of Surgery 238(4):577-585, Oct. 2003.

Philipose, M., et al., "Battery-Free Wireless Identification and Sensing," Pervasive Computing 37-45, Jan.-Mar. 2005, 9 pages.

"Robotics: Technologies and Global Markets," BCC Research, Feb. 2013, <http://www.bccresearch.com/market-research/engineering/robotics-market . . . > [retrieved Jan. 26, 2015], 2 pages.

(56) References Cited

OTHER PUBLICATIONS

Schaffer, J.M., et al., "Infectious Complications After Pulsatile-Flow and Continuous-Flow Left Ventricular Assist Device Implantation," Journal of Heart and Lung Transplantation 30(2):164-174, Feb. 2011.
Schocken, D.D., et al., "Prevention of Heart Failure: A Scientific Statement From the American Heart Association Councils on Epidemiology and Prevention, Clinical Cardiology, Cardiovascular Nursing, and High Blood Pressure Research; Quality of Care and Outcomes Research Interdisciplinary Working Group; and Functional Genomics and Translational Biology Interdisciplinary Working Group," Circulation 117(19):2544-2565, May 2008.
Siegenthaler, M.P., et al., "The Jarvik 2000 is Associated With Less Infections Than the HeartMate Left Ventricular Assist Device," European Journal of Cardio-Thoracic Surgery 23(5):748-755, May 2003.
Slaughter, M.S., and T.J. Myers, "Transcutaneous Energy Transmission for Mechanical Circulatory Support Systems: History, Current Status, and Future Prospects," Journal of Cardiac Surgery 25(4):484-489, Jul. 2010.
Thoratec Corporation, Form 10-K, United States Securities and Exchange Commission, Washington, D.C., Annual Report Under Section 13 or 15(D) of the Securities Exchange Act of 1934, Fiscal Year ended Jan. 1, 2011, 108 pages.
Van Der Zee, B., and A. Vaughan, "Nissan's Plug-Free Electric Car," The Guardian, Jul. 20, 2009, (http://www.theguardian.com/business/2009/jul/20/nissan-electric-car-plug . . . > [retrieved Jan. 22, 2015], 2 pages.
"Ventricular Assist Device," Wikipedia, the free encyclopedia, Jan. 1, 2015, <http://en.wikipedia.org/wiki/Ventricular_assist_device> [retrieved Jan. 22, 2015], 16 pages.
Waters, B.H., et al., "Innovative Free-Range Resonant Electrical Energy Delivery System (FREE-D System) for a Ventricular Assist Device Using Wireless Power," ASAIO Journal 60(1):31-37, Jan.-Feb. 2014.
Weingartner, M., "Wireless Power—Wireless Resonant Energy Link (WREL)," Intel, Jul. 1, 2010, <http://newsroom.intel.com/docs/DOC-1119> [retrieved Jan. 22, 2015], 2 pages.
Deng, M., et al., "Mechanical Circulatory Support Device Database of the International Society for Heart and Lung Transplantation: First Annual Report-2003," Journal of Heart and Lung Transplantation 22(6):653-662, Jun. 2003.
El-Banayosy, A., et al., "Preliminary Experience With the LionHeart Left Ventricular Assist Device in Patients With End-Stage Heart Failure," Annals of Thoracic Surgery 75(5):1469-1475, May 2003.
Extended European Search Report dated Jan. 5, 2016, issued in corresponding European Application No. EP13793259, filed May 21, 2013, 6 pages.
Frickey, D.A., "Conversions Between S, Z, Y, H, ABCD, and T Parameters Which are Valid for Complex Source and Load Impedances," IEEE Transactions on Microwave Theory and Techniques 42(2):205-211, Feb. 1994.
Gordon, R.J., et al., "Ventricular Assist Device-Related Infections," Lancet: Infectious Diseases 6(7):426-437, Jul. 2006.
Haj-Yahia, S., et al., "Midterm Experience With the Jarvik 2000 Axial Flow Left Ventricular Assist Device," Journal of Thoracic and Cardiovascular Surgery 134(1):199-203, Jul. 2007.
Holman, W.L., et al., "Device Related Infections: Are We Making Progress?" Journal of Cardiac Surgery 25(4):478-483, Jul. 2010.
Imura, T., "Study on Maximum Air-Gap and Efficiency of Magnetic Resonant Coupling for Wireless Power Transfer Using Equivalent Circuit," Proceedings of the IEEE International Symposium on Industrial Electronics, Bari, Italy, Jul. 4-7, 2010, pp. 3664-3669.
International Search Report and Written Opinion dated Aug. 26, 2013, issued in corresponding International Application No. PCT/US2013/042085, filed May 21, 2013, 9 pages.
Kim, N.Y., et al., "Adaptive Frequency With Power-Level Tracking System for Efficient Magnetic Resonance Wireless Power Transfer," Electronics Letters 48(8):1-2, Apr. 2012.

Kurs, A., et al., "Wireless Power Transfer Via Strongly Coupled Magnetic Resonances," Science 317(5834):83-86, Jul. 2007.
Low, Z.N., et al., "Design and Test of a High-Power High-Efficiency Loosely Coupled Planar Wireless Power Transfer System," IEEE Transactions on Industrial Electronics 56(5):1801-1812, May 2009.
Martin, S.I., et al., "Effect of Body Mass Index and Device Type of Infection in Left Ventricular Assist Device Support Beyond 30 Days," Interactive Cardiovascular and Thoracic Surgery 11(1):20-30, Jul. 2010.
McSpadden, J.O., et al., "Space Solar Power Programs and Microwave Wireless Power Transmission Technology," IEEE Microwave Magazine 3(4):4-57, Dec. 2002.
Miller, L.W., et al., "Use of a Continuous-Flow Device in Patients Awaiting Heart Transplantation," New England Journal of Medicine 357(9):885-896, Aug. 2007.
Mizannojehdehi, A.,et al., "Design and Analysis of a Class-E Frequency-Controlled Transcutaneous Energy Transfer System," Proceedings of the 13th IEEE International Conference on Electronics, Circuits and Systems, Nice, France, Dec. 10-13, 2006, pp. 21-24.
Monkowski, D.H., et al., "Infections Associated With Ventricular Assist Devices: Epidemiology and Effect on Prognosis After Transplantation," Transplant Infectious Disease 9(2):114-120, Jun. 2007.
Ozeki, T., et al., "Functions for Detecting Malposition of Transcutaneous Energy Transmission Coils," ASAIO Journal 49:469-474, Jul. 2003.
Pagani, F.D., et al., "Extended Mechanical Circulatory Support With a Continuous-Flow Rotary Left Ventricular Assist Device," Journal of the American College of Cardiology 54(4):312-321, Jul. 2009.
Park, J., et al., "Investigation of Adaptive Matching Methods for Near-Field Wireless Power Transfer," IEEE Transactions on Antennas and Propagation 59(5):1769-1773, May 2011.
Park, J.H., et al., "Optimum Frequency of High Q-Factor Resonator for Magnetic Resonance Coupling," Proceedings of the 41st European Microwave Conference (EuMC), Manchester, U.K., Oct. 10-13, 2011, pp. 61-63.
Raval, P., et al., "A Wireless Power Transfer System for Low Power Electronics Charging Applications," Proceedings of the Sixth IEEE Conference on Industrial Electronics and Applications (ICIEA), Beijing, Jun. 21-23, 2011, pp. 520-525.
Raymond, A.L., "Obesity and Left Ventricular Assist Device Driveline Exit Site Infection," ASAIO Journal 56(1):57-60, Jan.-Feb. 2010.
Sample, A.P., et al., "Analysis, Experimental Results, and Range Adaptation of Magnetically Coupled Resonators for Wireless Power Transfer," IEEE Transactions on Industrial Electronics 58(2):544-554, Feb. 2011.
Sample, A.P.,et al., "Enabling Seamless Wireless Power Delivery in Dynamic Environments," Proceedings of the IEEE 101(6):1343-1358, Jun. 2013.
Sample, A., et al., "Experimental Results With two Wireless Power Transfer Systems," Proceedings of the IEEE Radio and Wireless Symposium, San Diego, Jan. 18-22, 2009, pp. 16-18.
Smith et al., "Innovative Free-Range Resonant Electrical Energy Delivery System (Free-D System) for a Ventricular Assist Device Using Wireless Power," ASAIO Journal 60(1):31-37, Jan.-Feb. 2014 (Abstract only).
Sun, Y., et al., "Design Method for Impedance Matching Networks," IEEE Proceedings—Circuits, Devices and Systems 143(4):186-194, Aug. 1996.
Thompson, M., and J.K. Fidler, "Determination of the Impedance Matching Domain of Impedance Matching Networks," IEEE Transactions on Circuits and Systems—I: Regular Papers 51(10):2098-2106, Oct. 2004.
Topkara, V.K., et al., "Infectious Complications in Patients With Left Ventricular Assist Device: Etiology and Dutcomes in the Continuous-Flow Era," Annals of Thoracic Surgery 90(4)1270-1277, Oct. 2010.
Waters, B.H., et al., "Adaptive Impedance Matching for Magnetically Coupled Resonators," Proceedings of the Progress in Electromagnetics Research Symposium (PIERS), Moscow, Aug. 19-23, 2012, pp. 694-701.

(56) References Cited

OTHER PUBLICATIONS

Waters, B.H., et al., "Powering a Ventricular Assist Device (VAD) With the Free-Range Resonant Electrical Energy Delivery (Free-D) System," Proceedings of the IEEE 100(1):138-149, Jan. 2012.
Wilson, W., et al., "Prevention of Infective Endocarditis: Guidelines From the American Heart Association," JADA 139:3S-24S, 2008.
Zierer, A., et al., "Late-Onset Driveline Infections: The Achilles' Heel of Prolonged Left Ventricular Assist Device Support," Annals of Thoracic Surgery 84(2):515-521, Aug. 2007.
Extended European Search Report dated Jul. 26, 2017, issued in related European Application No. EP 17173137.5, filed May 21, 2013, 6 pages.
International Search Report and Written Opinion dated Oct. 23, 2015, issued in corresponding International Application No. PCT/US2015/42941, filed Jul. 30, 2015, 10 pages.

\* cited by examiner

WIRELESS POWER DELIVERY IN DYNAMIC ENVIRONMENTS

CROSS-REFERENCES TO RELATED APPLICATIONS

This application is a continuation of U.S. application Ser. No. 14/402,660, filed Nov. 20, 2014, which is a U.S. National Stage of PCT/US2013/042085, filed May 21, 2013, which is a continuation of U.S. application Ser. No. 13/843,884, filed Mar. 15, 2013 (U.S. Pat. No. 8,827,889, issued Sep. 9, 2014), which claims the benefit of Provisional Patent Application No. 61/734,236, filed Dec. 6, 2012, Provisional Patent Application No. 61/691,127, filed Aug. 20, 2012, and Provisional Patent Application No. 61/649,496, filed May 21, 2012, each of which are hereby incorporated by reference in their entireties.

BACKGROUND

Wireless power transfer using inductive coupling is becoming increasingly popular for consumer electronic devices. Commercial applications include wireless charging pads, electronic toothbrushes, induction cookers, and electric car battery chargers. However, none of these applications enable the range or geometric freedom that the term wireless power suggests. Charging pads and electric toothbrushes require that the device be placed very close to (or directly on top of) the charging pad. This is because the efficiency for traditional inductively coupled wireless power transfer systems drops off rapidly as the distance between the transmitter and receiver increases.

Far-field wireless power transfer techniques use propagating electromagnetic waves and are capable of delivering power to a much larger volume of space. However, there is an inherent tradeoff between directionality and transfer efficiency. For example, radio frequency (RF) broadcast methods—which transmit power in an omni-directional pattern—allow for power transfer anywhere in the coverage area. Although mobility is maintained, end-to-end efficiency is lost because the power density decreases with the square of the distance. Microwave systems with high gain antennas have been used to transfer power over several kilometers at efficiencies of over 90%. However, these systems suffer from the need for sophisticated tracking and alignment equipment to maintain a line of sight (point-to-point) connection.

Regulatory restrictions limit the amount of power that can be transmitted in uncontrolled environments for safety as well as emissions and interference reasons. As a result, the main commercial use of far-field wireless power transfer is for passive (i.e., battery free) UHF RFID tags which are limited to four watts equivalent isotropic radiated power in the USA.

Recent research efforts using magnetically coupled resonators (MCRs) for wireless power transfer have demonstrated the potential to deliver power with more efficiency than far-field broad-cast approaches, and at longer ranges than traditional inductively coupled methods. These techniques use high quality factor ("high-Q") coupled resonators that transfer energy via magnetic fields that do not strongly interact with the human body. U.S. Patent Publication No. 2012/0153738, to Karalis et al., and U.S. Patent Publication No. 2012/0080957, to Cooper et al., both of which are hereby incorporated by reference in their entireties, disclose certain aspects of wireless energy transfer using MCRs.

However, a drawback of current MCR systems is the inability to efficiently adapt to changes in the environment. For example, unpredictable loads and changes in distance and orientation between MCR coils rapidly change system operating points, which disrupt the end-to-end wireless power transfer efficiency. Dynamic adaptation of a system to these types of events is a critical capability in developing fully functional and versatile wireless power solutions.

FIG. 1 shows a diagram of a basic prior art wireless power system 90 using high-Q MCRs. A transmitter module 91 includes a single turn drive loop 93 and a multi-turn, spiral resonator or transmit coil (Tx coil) 94. When an RF amplifier 92 drives current through the drive loop 93 at the transmitter module's 91 resonant frequency, the resulting oscillating magnetic field excites the Tx coil 94. The Tx coil 94 stores energy in the same manner as a discrete LCR tank. This results in a large oscillating magnetic field in the vicinity of the Tx coil 94. A high-Q coil implies that more energy can be stored on the coil, which also results in greater magnetic flux density at a given point in space.

The receiver module 95 is designed similarly. It includes a multi-turn, spiral resonator or receive coil (Rx coil) 96 and a single turn load loop 97, which is connected to an end device 98. The drive loop 93 and Tx coil 94 are magnetically coupled, and the load loop 97 and Rx coil 96 are magnetically coupled. Similarly, the Tx coil 94 and the Rx coil 96 share a mutual inductance, which is a function of the geometry of the coils 94, 96 and the distance between them. The high-Q Tx and Rx coils 94, 96 form a single system of coupled resonators, which can efficiently transfer energy back and forth.

In generally and other parameters being held constant, the coupling coefficient between the Tx coil 94 and the Rx coil 96 is inversely proportional to the distance between the coils 94, 96. At relatively short distances (in the over-coupled regime) high efficiency power transfer between the coils 94, 96 can be achieve over a wide frequency range. As the separation distance increases, the coupling between the resonators 94, 96 decreases, and the frequency range for high efficiency power transfer narrows, until the optimal frequency converges to the fundamental frequency of the system (critical coupling). In the over-coupled regime, the resonators 94, 96 share more magnetic flux than is required to source the load. However, as discussed below, proper tuning techniques will enable near constant power transfer efficiency substantially within the entire over-coupled regime.

In the under-coupled regime, the shared flux falls below a critical point. Below this point, the Tx coil 94 needs to emit more power to maintain the magnetic field than can be absorbed by the Rx coil 96. The result is that maximum efficiency cannot be achieved. Critical coupling is the point of transition between these two regimes and corresponds to the greatest range at which maximum efficiency can still be achieved. The under-coupled regime is still capable of wireless power transfer, but efficiency decreases rapidly as distance increases.

A system is disclosed that takes advantage of the over-coupled regime to create a volume of space providing high efficiency power transfer between the transmitter module 91 and the receiver module 95, to wirelessly provide power to the end device 98. The system has also been found to provide range extension in the under-coupled region.

The coupling coefficient between the Tx coil 94 and the Rx coil 96 depends of operating frequency. Prior art systems have proposed maintaining high efficiency in transferring energy in an MCR system using dynamic frequency tuning.

The goal of dynamic frequency tuning is to automatically adjust the transmitter frequency (e.g., amplifier 92) to provide maximum power transfer efficiency between the Tx coil 94 and the Rx coil 96, e.g., as a user moves the Rx coil 96 within the system's working range.

The mutual inductance between the Tx coil 94 and the Rx coil 96 is a function of the coil geometry and the distance and orientation between the coils 94, 96. Although it is possible to transfer wireless power without adaptive techniques, small changes in distance between the transmitter and the receiver will generally cause very large changes in efficiency. However, by dynamically adapting the amplifier 92 frequency, a relatively large region of space can be accommodated for high efficiency power transfer.

However, in many applications adaptive frequency tuning is not a viable approach for high efficiency power transfer, in part because of governmental regulation of the frequency spectrum. Narrow bandwidth operation is desirable for regulatory reasons. Spectrum use regulations vary from country to country. Currently no country has allocated spectrum specifically for wireless power transfer. However, Industrial, Scientific, and Medical (ISM) bands are allocated internationally for RF applications other than communication. ISM bands are currently used for applications such as RF heating and microwave ovens. Therefore, they are a natural choice for today's wireless power transfer systems.

The ISM bands are governed in the U.S. by Part 18 of the Federal Communication Commission (FCC) rules. Part 15 of the FCC rules covers communication, even if the communication occurs in an ISM band. The field strength limits of Part 15 are more stringent than those of Part 18. Therefore, it may be desirable for wireless power transfer systems not to use the same band for power transfer and communication.

Existing ISM bands are too narrow to accommodate frequency tuning. For example, in a particular test system the bandwidth requirements of dynamic frequency tuning exceed the available bandwidth from FCC regulations by three orders of magnitude.

The present invention includes methods and systems for an MCR power transfer system that dynamically adapts to variations in range, orientation, and load using both wideband and fixed-frequency techniques. In particular, impedance matching methods and systems are disclosed that are suitable for fixed frequency operation, adaptive frequency tuning for wider bandwidth systems, and adaptive load matching techniques utilizing maximum power point tracking.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

An adaptive impedance matching wireless power transfer system includes a drive inductor configured to receive RF power, a first high-Q resonator coil inductively coupled to the drive inductor, a second high-Q resonator coil inductively coupled to the first high-Q resonator coil, and a load inductor inductively coupled to the second high-Q resonator coil. A first matching network, for example a π-match network or an L-match network, is operably coupled to either the drive inductor or the load inductor, and is configured to selectively adjust the impedance between the drive or load inductor and the corresponding resonator coil. In an embodiment the drive or load inductor is the inductor for the first matching network. In an embodiment the drive inductor and/or the load inductor comprise a single loop.

In an embodiment the first matching network is a π-match network with variable capacitances, which may be implemented, for example with one or more banks of capacitors configured in a switchable network. In an embodiment the switchable network is controlled with a microcontroller that selectively engages one or more of the capacitors in the bank of capacitors, to thereby adjust the impedance between the inductor and the resonator coil.

In an embodiment, the microcontroller adjusts the capacitors to maximize the forward transmission gain to the transmitter coil, for example using an exhaustive search through available switch combinations, using lookup tables correlating a measurable parameter of the system, or using a measured performance parameter of the system.

In an embodiment the system further comprises a second π-match network, wherein the first matching network is operably connected to the drive inductor and the second matching network is operably connected to the load inductor.

In an embodiment the system further comprises a rectifier with an active impedance matching circuit configured to receive direct current from the rectifier, and a microcontroller configured to monitor the direct current from the rectifier and to control the active impedance matching circuit to selectively harvest power from the rectifier and provide power to a device.

An adaptive impedance matching wireless power transfer system includes a transmit side comprising a drive inductor configured to receive alternating current electric power from a power source at a fixed frequency, and a high-Q transmitter coil inductively coupled to the drive inductor, and a receive side comprising a high-Q receiver coil configured to be inductively coupled to the transmitter coil, and a load inductor inductively coupled to the receiver coil. A first matching network comprising a plurality of capacitors interconnected to form a switchable bank of capacitors, and a microcontroller operably connected to the switchable bank of capacitors, wherein the microcontroller is configured and operable to receive a measured operating parameter of the adaptive impedance matching wireless transfer system and to use the measured parameter to selectively adjust the impedance between either (i) the drive inductor and the transmitter coil, or (ii) the load inductor and the receiver coil.

In an embodiment the measured parameter comprises an S-parameter or an RMS voltage measured in the system.

In an embodiment the measured parameter is measured on the transmit side, and the microcontroller selectively adjusts the impedance between the drive inductor and the transmitter coil.

In an embodiment the measured parameter is measured on the receive side, and the microcontroller selectively adjusts the impedance between the load inductor and the receiver coil.

In an embodiment the measured parameter is measured on the receive side, and the microcontroller selectively adjusts the impedance between the drive inductor and the transmitter coil.

In an embodiment the measured parameter is measured on the transmit side, and the microcontroller selectively adjusts the impedance between the load inductor and the receiver coil.

In an embodiment the first matching network is operably connected to the transmit side, and further comprising a second matching network comprising a plurality of capacitors interconnected to form a switchable bank of capacitors, and a second microcontroller operably connected to the switchable bank of capacitors, wherein the second microcontroller is configured and operable to receive a measured operating parameter of the adaptive impedance matching wireless transfer system and to use the measured parameter to selectively adjust the impedance between the load inductor and the receiver coil.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A system and method for the wireless power transmission that take advantage of the unique properties of magnetically coupled resonators (MCRs) is disclosed. A detailed description of the operating principles and performance characteristics of MCRs is presented in "Analysis, Experimental results, and range adaptation of magnetically coupled resonators for wireless power transfer," A. Sample, D. Meyer and J. Smith, *Industrial Electronics, IEEE Transactions on*, Vol. 58, No. 2, pp. 544-554, February 2011, which is hereby incorporated by reference in its entirety. A brief overview of system features that can enable seamless wireless power delivery is provided to facilitate an understanding of the present invention.

A wireless power transfer system is disclosed that uses high-Q magnetically coupled resonators, and one or more dynamic impedance matching networks to maintain high power transfer efficiency between the resonators within a very narrow frequency band, or at a single predetermined frequency.

Figure 1:
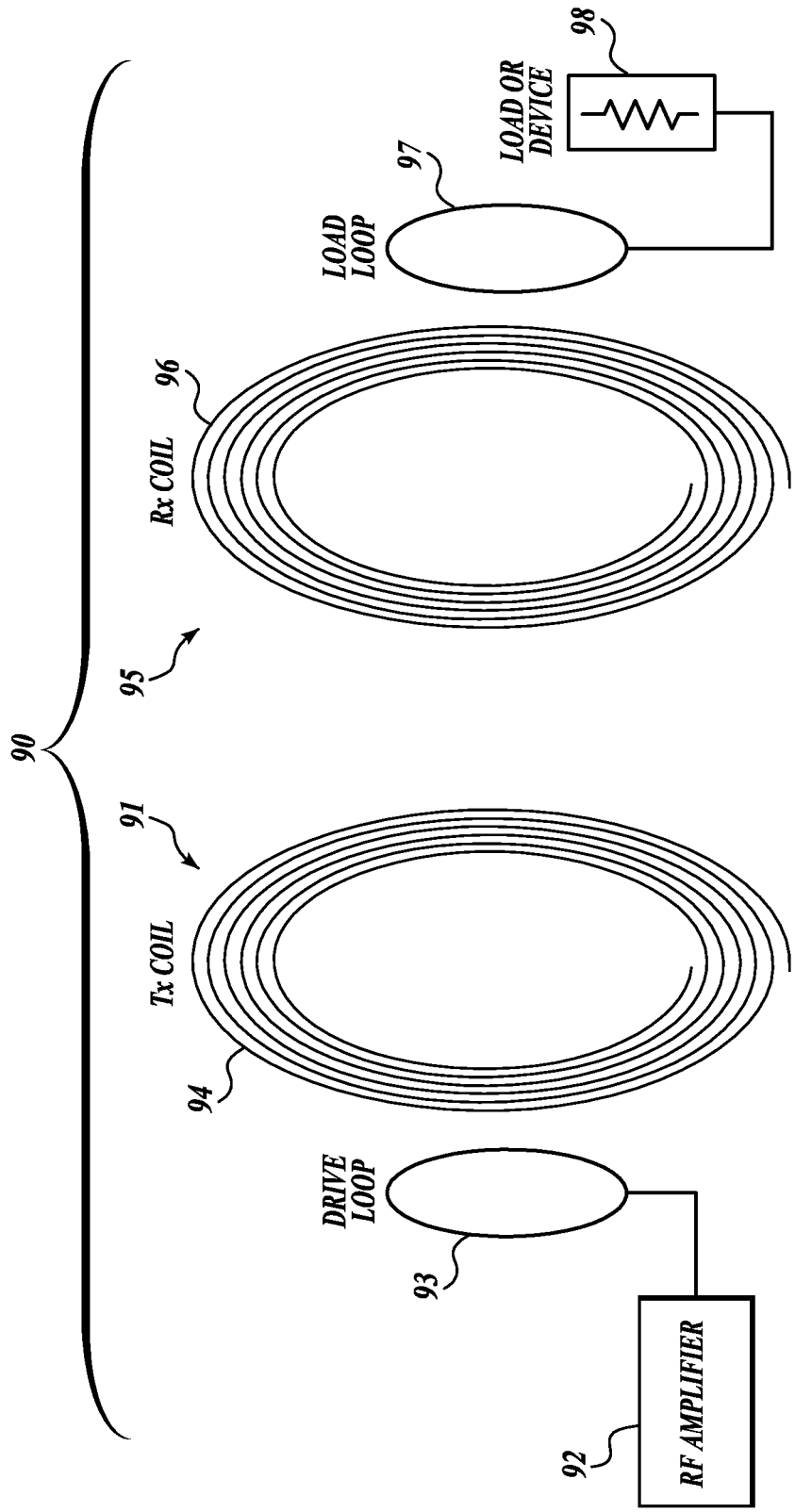
FIG. 1 illustrates a basic prior art wireless power system using magnetically coupled resonators.

It will be appreciated that the input impedance of the prior art MCR wireless power system 90 shown in FIG. 1 will vary due to changes in the location and/or orientation of the Tx and Rx resonator coils 94, 96 because the mutual inductance between the Tx coil 94 and the Rx coil 96 varies as a function of distance and orientation. Additionally, when the Tx and Rx coils 94, 96 are sufficiently close to each other, the cross coupling and direct capacitance feed through from one coil can detune the opposite coil and reduce the quality factor Q of each MCR. Both of these factors contribute to a mismatch between source and load impedance that substantially degrades power transfer efficiency.

With the system 90 the detuning effect or drop in efficiency may be overcome by varying the loop-to-coil geometry, and therefore the coupling coefficient $k_{lc}$. However, this method of tuning $k_{lc}$ is not preferred because it requires mechanically adjusting the distance between each loop 93, 97 and its corresponding coil 94, 96.

Figure 2A:
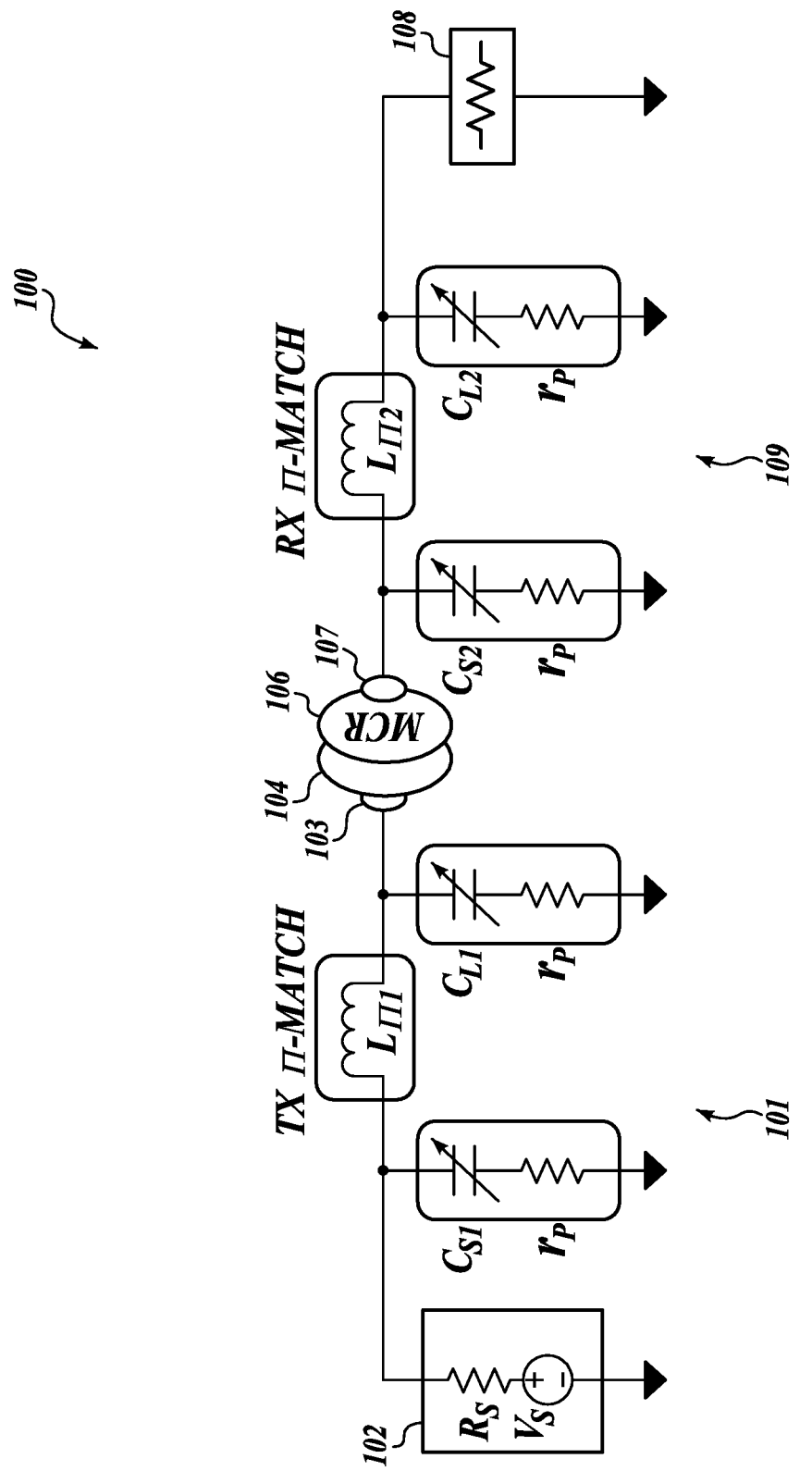
FIG. 2A is a block diagram illustrating schematically a wireless power system for dynamic impedance matching in accordance with the present invention.

The present inventors disclose a method and system for achieving high efficiency narrowband operation by adding dynamic impedance matching networks to one or both of the drive loop 93 and the load loop 97. A block diagram of a wireless power system 100 for dynamic impedance matching is shown in FIG. 2A.

Figure 2B:
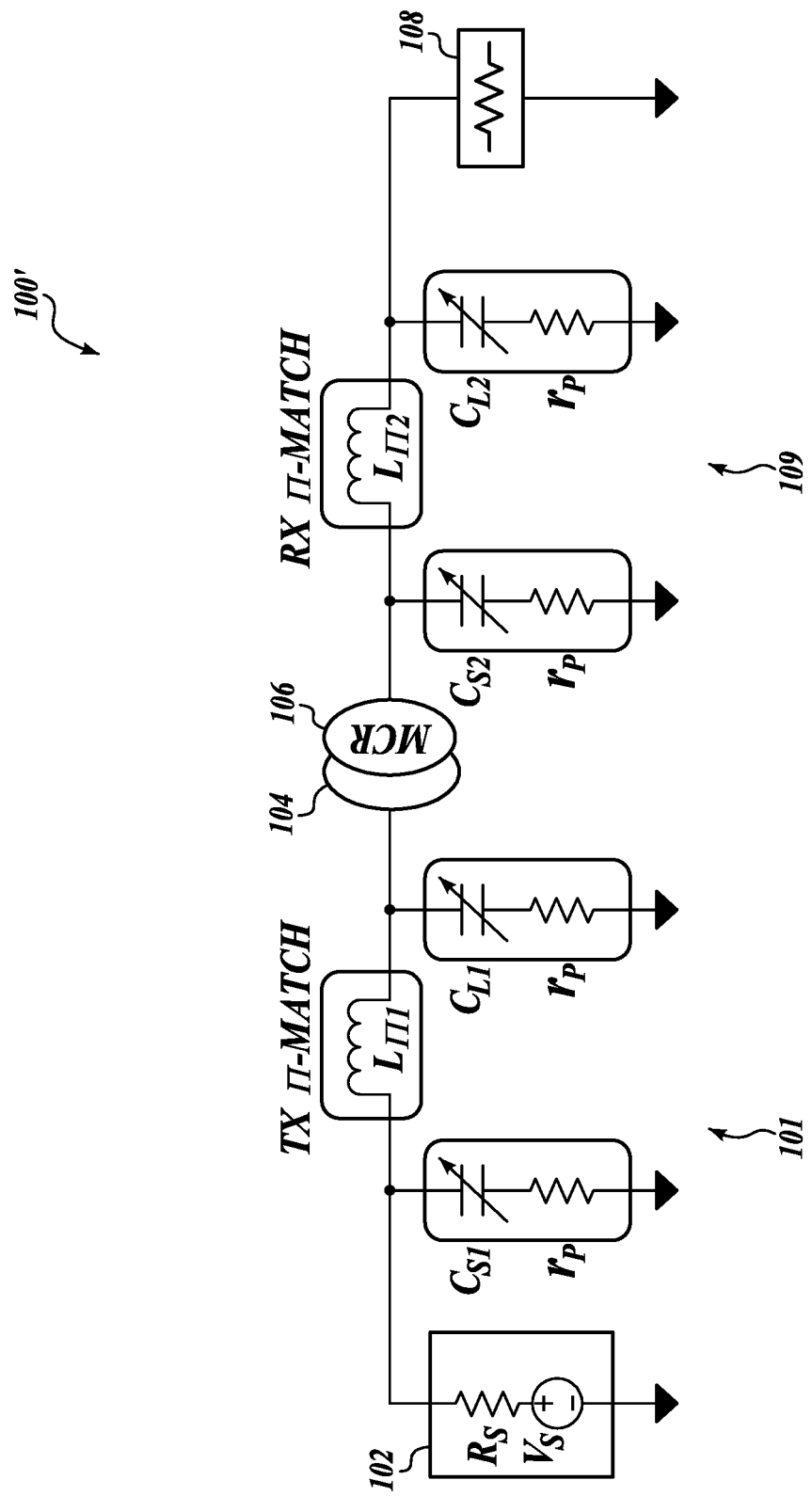
FIG. 2B is a block diagram similar to that shown in FIG. 2B, wherein the drive loop and load loop function is provided by the inductors in the matching networks.

FIG. 2B is a block diagram illustrating an alternative system 100' wherein the drive loop 103 and the load loop 107 are functionally replaced by the π-match networks 101, 109, respectively, with the corresponding inductor Lπ1, Lπ2 serving at the drive and/or load loop(s).

In the wireless power system 100 a first or Tx adjustable π-match network 101 is provided between an amplifier 102 and a drive loop 103 that is magnetically coupled to a high-Q MCR Tx coil 104. A second or Rx adjustable π-match network 109 is provided between a load loop 107 coupled to an MCR Rx coil 106 and an end device 108. In this embodiment, the topology includes variable capacitors $C_{S1}$, CL1 and a fixed inductor Lπ1 with the parasitic equivalent series resistance $r_p$) on the transmit side, and variable capacitors $C_{S2}$, $C_{L2}$ and a fixed inductor Lπ2 on the receive side. The transmit side inductor Lπ1 (for the first adjustable π-match network 101) and the receive side inductor Lπ2 (for the second adjustable π-match network 109) may have different inductance values.

This wireless power system 100 performs dynamic impedance matching by dynamically controlling the variable capacitances of both π-match networks 101, 109. Other matching networks, for example L-match networks, may alternatively be used and are contemplated by the present invention. However, compared to other matching network topologies the π-match network is currently preferred for adaptive wireless power transfer. The π-match network has several advantages, for example the π-match network uses a fixed-value inductor in the high-current path, and variable capacitors that handle relatively low power in shunt configurations. Also, the π-match network is able to match source impedances that are both greater than, equal to, and less than load impedances.

Although FIGS. 2A and 2B show matching networks on both the Tx side and the Rx side, it is contemplated that a system may be implemented with a matching network on only one side. It is a design consideration whether to place a matching network on both the Tx and Rx sides. The combination of the Tx π-match network 101 at the input to the drive loop 103 and the Rx π-match network 109 at the output from the load loop 107 provides a wider range of impedance matching between source and load impedances than would be available with either network 101, 109 alone, thus resulting in higher wireless power transfer efficiency at a single frequency for any separation distance. This is because in many instances π-match networks at both sides can do a better job of impedance matching when there is a large deviation between source and load termination impedances. A π-match network has an extra degree of freedom from the typical L-match network, and that is the Q factor of the matching network, which can be tuned to achieve a wideband or narrowband impedance match. In the L-match network, the Q factor of the matching network is fixed for a given impedance and capacitance. In a π-match network the same impedance match can be achieved for wide range of matching network Q factors.

Using unconstrained nonlinear optimization to determine the ideal capacitor values for π-match networks 101, 109 that will maximize the forward transmission gain S21 are determined for a range of coupling coefficients between the MCR coils 104, 106. The current method measures one or more of the scattering parameters, or S-parameters ([S] matrices) for one or both of Lπ1, Lπ2 and for the set of MCR coils 104, 106, and converts the S-parameters into ABCD-matrices, as is known in the art for two-port network analysis. The ABCD representation is convenient because a series of cascaded two-port networks can be modeled by computing the product of their individual ABCD matrices to form a single lumped ABCD-matrix for the system. The ABCD matrices for the Tx π-match network 101, the MCR coils 104, 106 and the Rx π-match network 109 are multiplied together. After converting the lumped ABCD-matrix back to an S-matrix, the source and load capacitor values in each π-match network 101, 109 are determined by selecting values that optimize [S21] at the desired frequency.

The method will now be described in more detail with reference to FIG. 3, for the system shown in FIG. 2A. The [S] matrices and the [Y] matrices for the components are obtained 200. The S-parameters for the set of MCRs may be obtained, in a number of ways, including for example, from manufacturer data, with a vector network analyzer, with a directional coupler, or the like. It is preferable to use measured data so that all of the parasitic effects are considered. Typically, the transfer functions for a 4-coil MCR system neglect parasitic effects such as cross-coupling and coil de-tuning that can significantly reduce efficiency at the resonant frequency. The admittance matrices [Y] are also defined for the capacitance components of the π-match networks 101, 109. Obtaining the [S] matrices and [Y] matrices is well within the abilities of persons of skill in the art.

The [S] and [Y] matrices are converted into [ABCD] transmission matrices 202. These [ABCD] matrices for the individual component are combined 204, e.g., by multiplying the cascaded [ABCD] matrices to define a system [ABCD] matrix. A system [S] matrix is calculated 206 from the system [ABCD] matrix using complex termination impedances to match a source impedance to a defined load impedance. Finally, a conventional constrained non-linear optimization algorithm may be used to determine the component values $C_{S1}$, $C_{L1}$, $C_{S2}$, $C_{L2}$ in each network 208 that maximize S21. Equivalently, the algorithm may minimize the reflection S-parameter, S11. It is also contemplated that the algorithm may be configured to maximize power transfer efficiency, if data from an out of band radio is available to communicate between the power transmit side and receive side.

Figure 4:
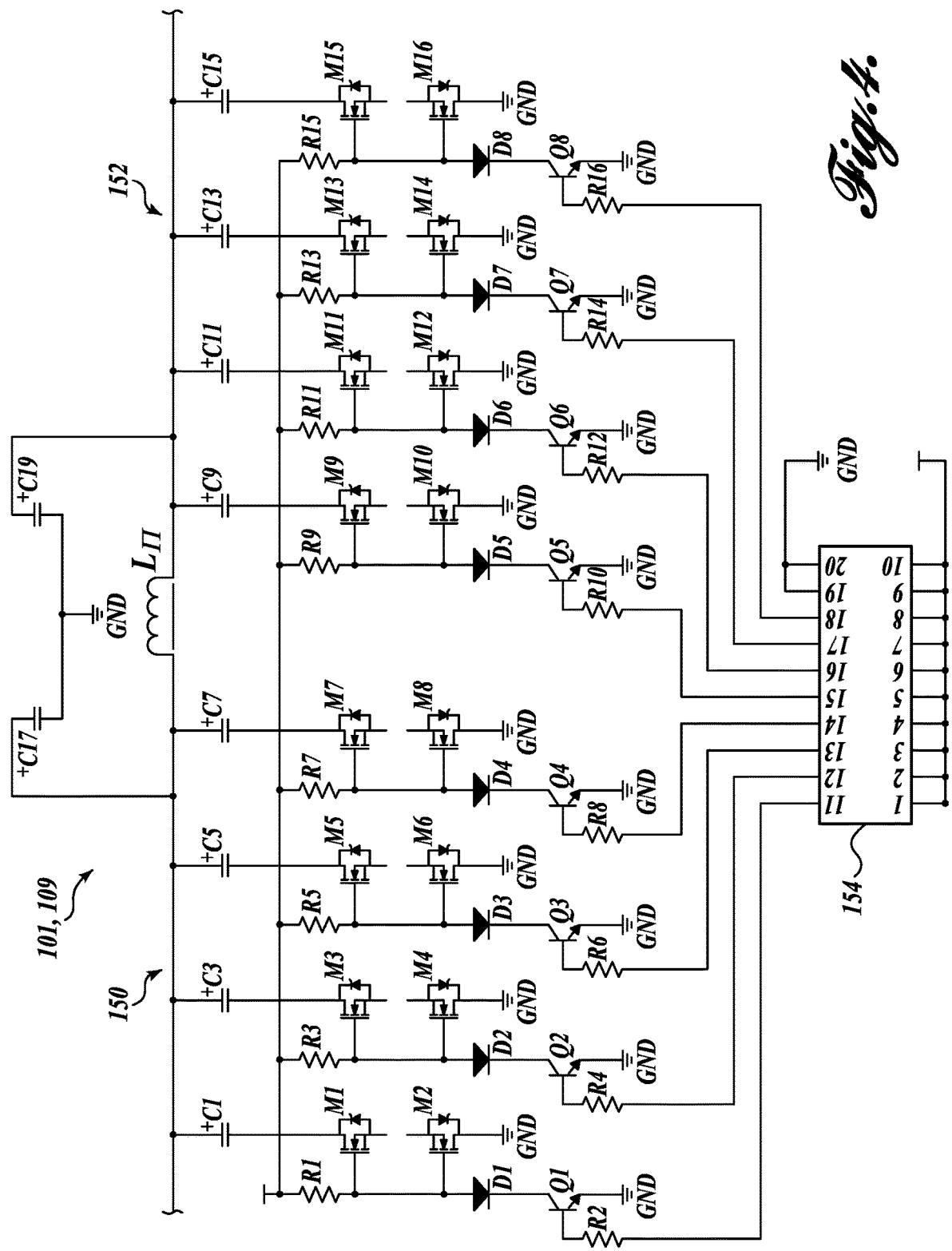
FIG. 4 is a circuit diagram for implementing a π-match network suitable for the system shown in FIG. 2A.

FIG. 4 illustrates an exemplary switching circuit that is suitable for implementing the first and/or second π-match networks 101, 109 shown in FIG. 2A. In this embodiment the variable capacitor $C_{S1}$ (or $C_{S2}$) is implemented with a plurality of fixed capacitors C1-C7, and the variable capacitor $C_{L1}$ (or $C_{L2}$) is implemented with a plurality of fixed capacitors C9-C15, wherein the capacitors C1-C15 are networked in switchable capacitor banks 150, 152. Each of the capacitors C1-C15 in the capacitor banks 150, 152 are selectively engaged through a network of controllable micro-switches M1-M16. A microcontroller 154 is configured to engage the desired capacitors, which are selected to approximately maximize S21.

In the example switching circuit shown in FIG. 4 the microcontroller 154 controls the capacitor banks 150, 152 through the switching circuit, which includes the microcontroller 154. The microcontroller 154 is operably connected to control a plurality of sub-circuits that engage an associated one of the capacitors C1-C15. The switching circuit is configured to selectively engage or disengage the associated one of the plurality of capacitors C1-C15 from the capacitor banks 150, 152. The switching circuit will be described with reference to engaging and disengaging capacitor C1. In this embodiment the controllable microswitches M1-M16 are field effect transistors, for example MOSFETs (metal-oxide semiconductor field-effect transistors). Each sub-circuit also includes a pair of back-to-back field effect transistors (e.g., M1 and M2) that connect the associated capacitor (e.g., C1) to a ground GND. The sub-circuits include a gate drive filter (e.g., R1, D1, Q1, R2) that is operatively controlled by the micro-processor 154 and configured to selectively switch the field effect transistors (e.g., M1, M2) between an open state and a closed state. In particular, the microcontroller 154 is configured to receive a measured operating parameter of the adaptive impedance matching wireless power transfer system (for example, an S-parameter, as described above) and to use the measured operating parameter to selectively adjust the impedance between the inductor Lπ and the associated MCR coil 104, 106 (FIG. 3).

Figure 3:
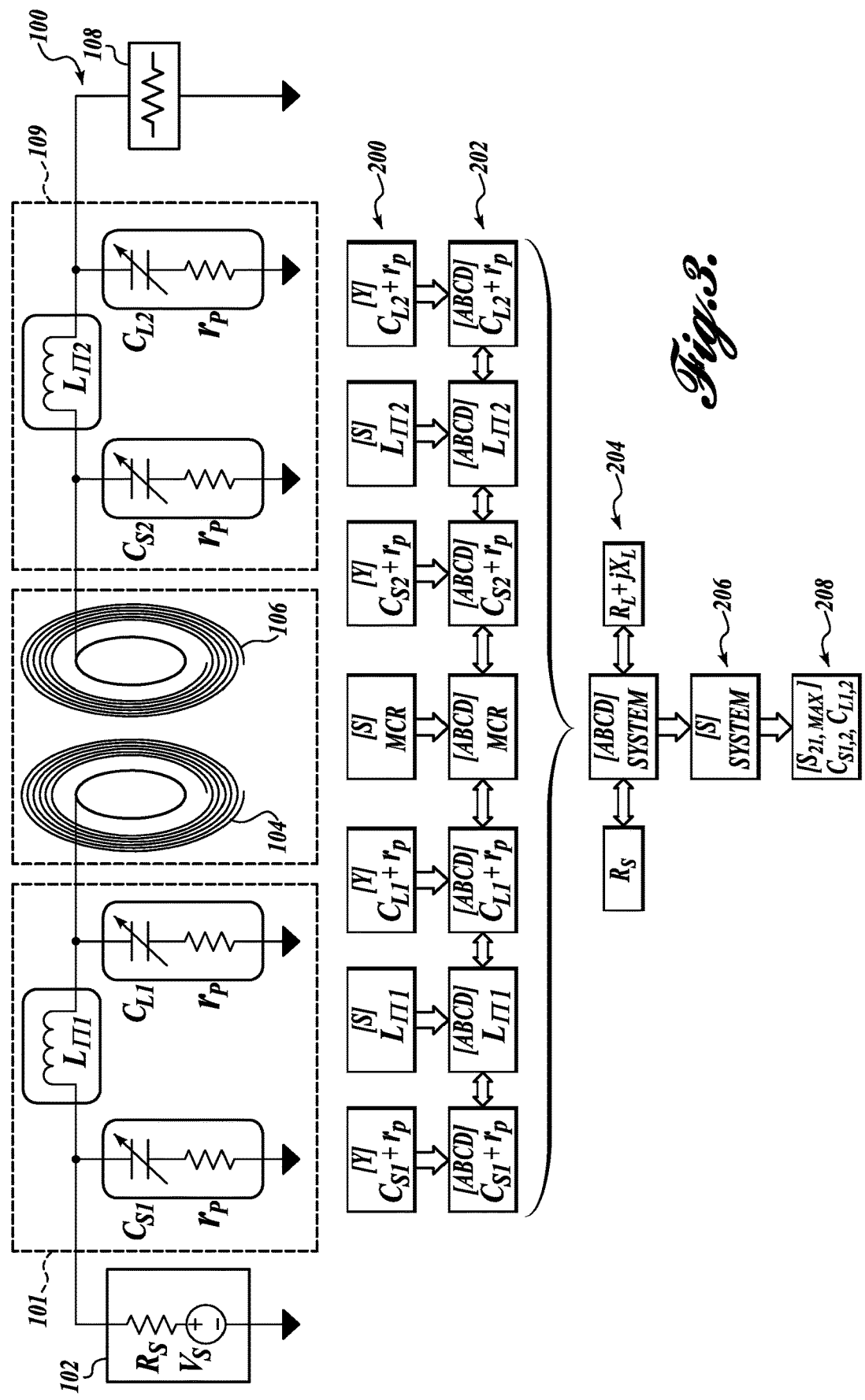
FIG. 3 illustrates a method for optimizing a wireless power system, for example that shown in FIG. 2A, for narrow band or single frequency operation.

In practice, it may be time consuming to determine the optimal values using the algorithm illustrated in FIG. 3. In an alternative embodiment, using the capacitor banks 150, 152 described above, a control algorithm may exhaustively sweep each possible combination of capacitor settings while monitoring one or more of the scatter parameters, and select the configuration that achieves minimum reflected power. For example, ten switchable shunt capacitors (five on each side of the inductor) have a topology with 1,024 possible states.

It is also contemplated, and will be apparent to persons of skill in the art, that other approximate methods may be selected to arrive at an optimal set of capacitor settings, in order to achieve more rapid switching in a dynamic environment. For example, the control algorithm may be configured to intelligently estimate the coupling coefficient between the two MCR coils, for example, by detecting the distance between the coils 104, 106. A table of the optimal component values representing the possible physical arrangements between the two MCR coils 104, 106 may be pre-calculated, and the physical positioning of the MCR coils may be used with a lookup table to control the optimal capacitor bank 150, 152 settings.

In another embodiment the power delivered to the load 108 (FIG. 2A) may be monitored at the receive side of the system, and an out of band radio link (not shown) may be used to report back to the control algorithm at the transmit side the status of the received power. The system may then automatically detect a change in distance or orientation between the MCRs 104, 106. Such changes could then be used to initiate a new sweep through the switch settings, i.e., when a change in the coupling coefficient is detected. In yet another embodiment, rather than an exhaustive sweep through the switching network the control algorithm may use a gradient approach to select only a subset of possible capacitor settings to find a local optimal transfer efficiency.

A significant challenge in developing effective wireless power systems is the efficient rectification of RF to DC power across the systems operating points. This issue arises from the desire to maintain optimal impedance matching between the receiving antenna and the rectifier as the impedance of the load for the application is changing. To maintain optimal power transfer while undergoing changes in the coupling coefficient between the MCR coils 104, 106 (which is affected by the distance and orientation between the source and the load, and by fluctuations in the load), an adaptive rectifier has been developed that uses a nonlinear impedance matching circuit element and control method to adapt to changes in the environment.

Figure 5:
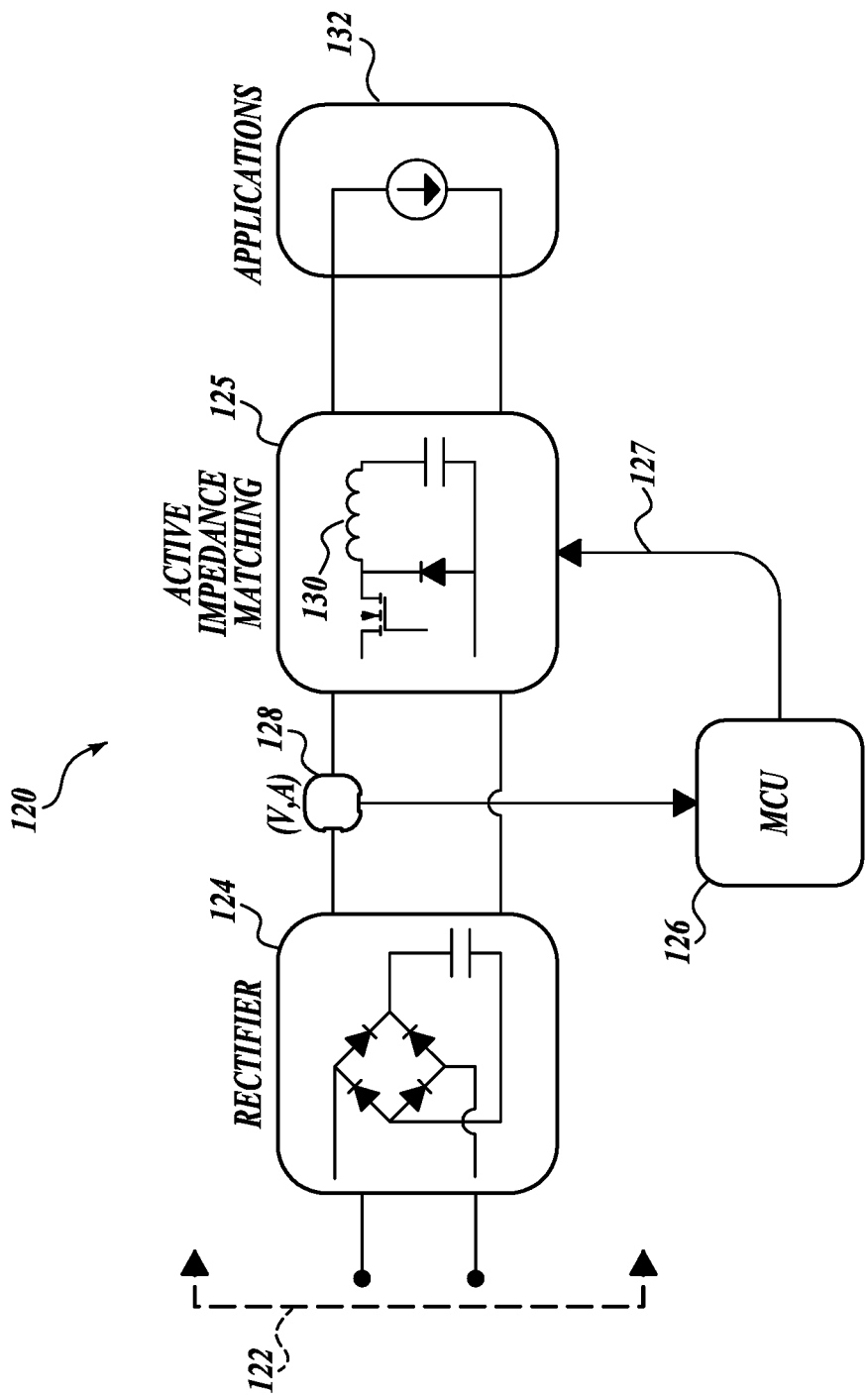
FIG. 5 is a diagram illustrating an adaptive rectifier system in accordance with the present invention, that is suitable for use with the system shown in FIG. 2A or for a power transfer system without adaptive impedance matching.

A diagram of the adaptive rectifier system 120 is shown in FIG. 5. In this exemplary embodiment, the power 122 from the Rx side second π-match network 109 (FIG. 2A) is provided to a full wave rectifier 124 that converts the RF power 122 to DC power. A dynamic impedance matching circuit 125 is controlled by a microcontroller 126 that receives input from conventional voltage and current sensing circuits 128 and generates a pulse width modulated (PWM) control signal 127. The impedance matching circuit 125 uses a feed-forward buck converter 130 to control the ratio of voltage to current that is drawn from the rectifier 124 and delivered to the load 132. Additional control algorithms and/or voltage regulation stages may be provided for a particular application.

The adaptive rectifier system 120 architecture and the control algorithms implemented on the microcontroller 126 is similar to Maximum Power Point Tracking (MPPT) techniques used for harvesting maximum power from solar cells. See, for example, U.S. Pat. No. 7,986,122, to Fornage et al., which is hereby incorporated by reference.

In a wireless power transfer system such as the system 100 described above (FIG. 2A), the output of the MCR Rx coil 106 and the π-match network 109 presents a variable source resistance. The typical application or load 108 will also present a variable load resistance. Thus adaptation techniques are beneficial to optimize power transfer.

The adaptive rectifier system 120 may comprise a full wave rectifier 124, over voltage protection (not shown), a high voltage synchronous NMOS driver (e.g., a high voltage synchronous N-channel MOSFET driver, such as the LTC® LTC4444 MOSFET driver available from Linear Technology Corporation, in Milpitas, Calif.), circuits for measuring voltage and current 128, and an microcontroller 126 that implements the control algorithm for tracking the maximum power point of the rectifier 124 (e.g., the MSP430™ ultra-low-power microcontroller available from Texas Instruments Incorporated, in Dallas, Tex.).

One commonly overlooked aspect of RF rectifier design is that the load impedance of the application is essentially transferred through the rectifier and impacts the impedance match between the RF antenna/coils and the input of the rectifier itself. Occasionally this apparent power loss to the load is interpreted as inefficiencies in the rectifier. However, the present inventors believe RF power is being reflected off of the rectifier-antenna interface.

For example, consider an RF amplifier connected to an ideal rectifier that is terminated into a 200 Ω load resistor. The ideal rectifier will not alter the ratio of voltage to current (characteristic impedance) passing through it, but will simply invert the negative portion of the incoming sine wave. Thus, when looking into the rectifier, the impedance seen is simply that of the 200 Ω resistor. Therefore, if the rectifier is driven by a source with 50Ω characteristic impedance, a portion of the incident wave will be reflected due to the mismatch between the 50 Ω to 200 Ω interface, resulting in an apparent power loss to the load. From this example it is clear that the loading conditions placed on the rectifier make a significant impact on the total power delivered to the load.

To illustrate the issue of load matching and to demonstrate the effectiveness of the new adaptive rectifier and the improvement made when the adaptive rectifier is enabled, an experiment was performed wherein the RF amplifier 102 (FIG. 2A) with a source impedance of 50 Ω is connected to the adaptive rectifier 124. The RF amplifier 102 sweeps its output power from 3-30 watts at a fixed frequency of 13.56 MHz. At each sweep point, an electronic load provided a second sweep of load current, which emulated different power consumption modes that an application might present. The resulting rectifier 124 output voltages and currents were recorded using a digital multimeter. A host computer running Labview® was used to control the system and record data.

When rectifier adaptive impedance matching 125 is turned off it was observed that under some loading conditions applied to the rectifier 124 an impedance mismatch occurs between the output of the coils and the input of the rectifier 124, and this mismatch results in poor power transfer. There is only a narrow operating range where optimal power transfer can be achieved.

When the adaptive impedance matching circuit 125 is enabled, the MSP430 microcontroller 126 measures the output voltage and current ratio delivered to the load 132. The control algorithm adjusts the PWM signal 127 that drives the feed-forward buck converter 130. This maximizes rectified power and thus maximizes the amount of power delivered to the load 132. For nearly any input power level and load current, an operating point can be found that maximizes power transfer, which resulted in a plateau of near constant transfer efficiency. The conclusion is that rectifiers that use MPPT techniques can effectively mitigate load variation, which would normally disrupt power transfer.

The above describes a method for controlling the apparent load impedance seen by the output of the rectifier 124 to optimize the RF power transfer. In effect, the loading condition on the rectifier 124 maintains the optimal impedance match between the input of the rectifier 124 and the output of the RF amplifier 102.

Another way to look at the system 100 is that if the source impedance of the amplifier 102 (or magnetically coupled resonators) is not 50Ω, the maximum power point tracking algorithm on the microcontroller 126 will still servo the PWM control signal 127 to maximize the power transfer. This will in turn change the input impedance to the rectifier 124 to closely match the output impedance of the amplifier 102. Thus the adaptive matching circuit block 125 can be used to control the real input impedance of the rectifier 124.

Controlling the duty cycle of the feed-forward buck converter 130 allows the adaptive rectifier to servo its input impedance. However, some reactance is introduced and the impedance matching is not purely real. This is believed to be due to the junction capacitance of the diodes. One possible improvement to the system, therefore, would be to mitigate this parasitic reactance with a switched impedance matching network. Ultimately, this shows that using a feed-forward buck converter 130 to form an adaptive rectifier is an effective means of electronically controlling the RF impedance of a rectifier 124 using only solid state devices.

Figure 6:
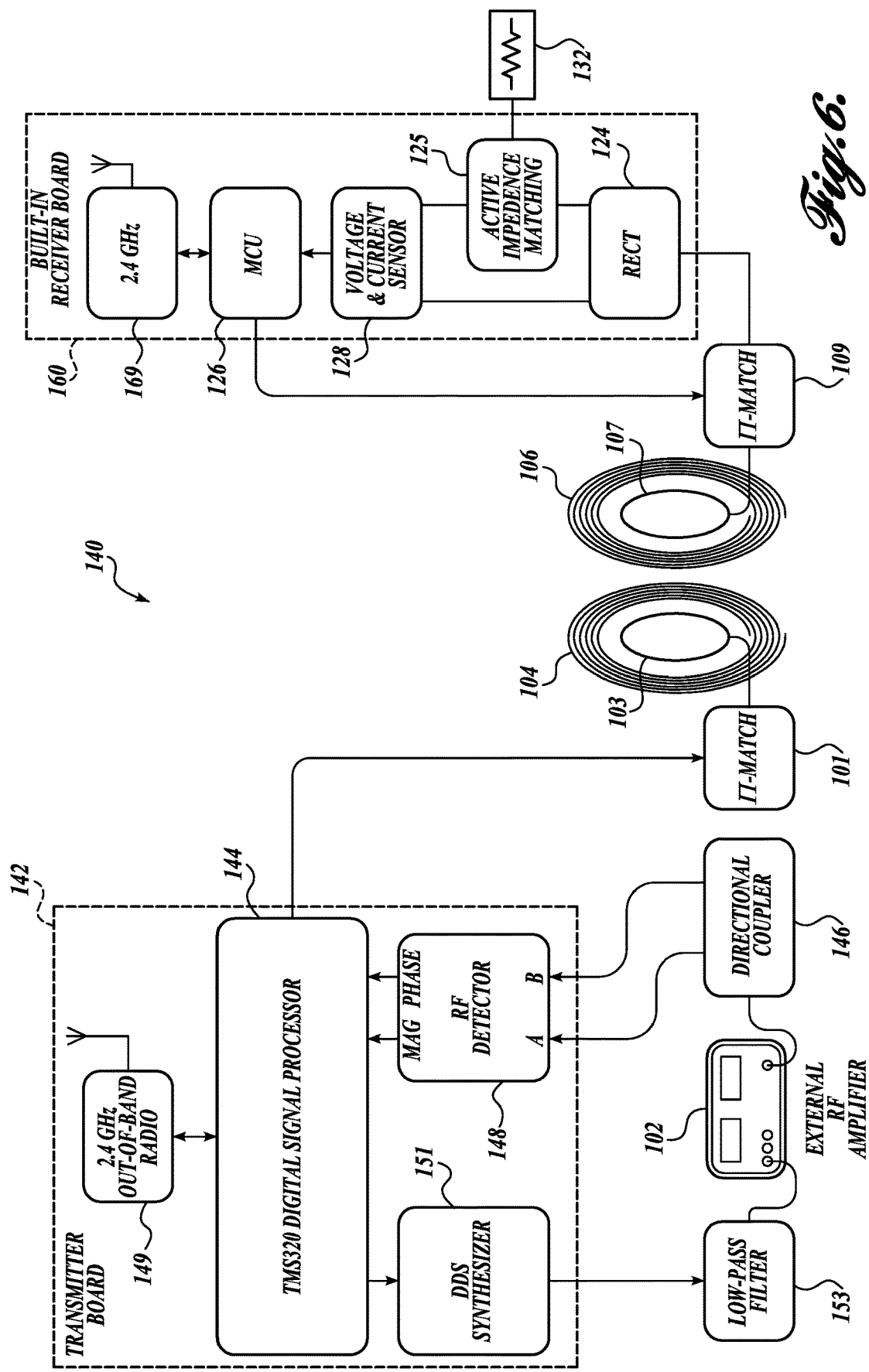
FIG. 6 is a block diagram illustrating another embodiment of a wireless power system in accordance with the present invention.

Another embodiment of a system 140 for adaptive wireless power transfer using MCRs shown in FIG. 6, which includes the MCR system shown in FIG. 2A, with π-match networks 101, 109 on both the Tx side and the Rx side. The system 140 includes a transmitter board 142 with a digital signal processor (DSP) 144 (e.g., a TMS320® DSP available from Texas Instruments Incorporated). The DSP 144 controls all peripherals on the transmitter board 142 and communicates with an external PC via a serial-to-USB chip (not shown). To detect how much power the system delivers to the load 132, the incident and reflected ports of a directional coupler 146 are attached to the inputs of an RF detector chip 148. The detector chip 148 outputs a voltage that is proportional to the log magnitude ratio and phase between incident and reflected power (i.e., 1/S11). For example, if the DSP 144 is clocked at 150 MHz it may take many digital samples in a short period of time. In fact, it only takes this system 140 about 5 µs to take one data point.

Using these measurements, the DSP 144 adjusts the transmit frequency of an RF synthesizer 151, which drives the amplifier 102 through a low-pass filter 153. Optionally, the system 140 may also employ dynamic impedance matching by controlling π-match boards 101, 109, for example, via parallel general purpose input/output ("GPIO") interfaces from the DSP 144. An external RF amplifier 102 is used to achieve an output power of up to 100 W in this exemplary embodiment. The receive side includes a receiver board 160 that may incorporate the rectifier system 120 shown in FIG. 5. Optionally, both the transmitter board 142 and the receiver board 160 include out-of-band radios 149, 169 (e.g., CC2500 transceivers available from Texas Instruments Incorporated), which implement out-of-band communication and allow the load to provide information about power consumption, position, or orientation, as well as control for a remote π-match board.

The system's 140 control algorithm chooses the optimal system parameters (π-match settings) given the current system state and maximizes power transfer over time as described above.

The system 140 is capable of fixed frequency operation using dynamic impedance matching. π-match boards 101, 109 contain capacitor banks that can be switched on or off by a parallel GPIO interface. The search space for actively controlling the π-match networks 101, 109 is more complicated than that of frequency tuning. Where frequency tuning's search space was one-dimensional, the space for impedance matching is two-dimensional, as the system can change both the Tx-side or Rx-side capacitances. Thus, the bank capacitor values should be chosen to provide the most effective matching circuit with the fewest number of capacitors. It is contemplated that for any given arrangement of MRC coils 104, 106 it may be determined that some capacitor settings will not correspond to optimal impedance matches, and may be excluded from the search space ahead of time.

Wireless power systems based on magnetically coupled resonators can realize the vision of seamless, reliable wireless power delivery if they are able to adapt to variations in range, orientation, and loading conditions. The key insight is that the over-coupled regime allows for high efficiency and near constant power delivery if the system is tuned properly.

In particular, we have demonstrated that adaptive impedance matching techniques used for fixed frequency operation can enable wireless power delivery to larger areas of space than previously published work. Additionally we have introduced an adaptive rectifier topology that is capable of adapting to changes in loading conditions to allow for optimal power delivery to the load. Conversely, the adaptive rectification technique also allows a receiver to control its input impedance to ensure proper matching to the magnetically coupled resonators. Finally, a full end-to-end system capable of adapting to real-time changes in the environment while maintaining optimum efficiency is disclosed.

While illustrative embodiments have been illustrated and described, it will be appreciated that various changes can be made therein without departing from the spirit and scope of the invention.

The embodiments of the invention in which an exclusive property or privilege is claimed are defined as follows:

1. An adaptive impedance matching wireless power transfer system comprising:
   a drive inductor configured to receive alternating current electric power from a power source at a fixed frequency;
   a high quality factor ("high-Q") transmitter coil inductively coupled to the drive inductor;
   a high-Q receiver coil configured to be inductively coupled to the transmitter coil; and
   a load inductor inductively coupled to the receiver coil;
   a first impedance matching network comprising a plurality of capacitors that are (i) operably coupled to the drive inductor and configured to selectively adjust the impedance between the drive inductor and the transmitter coil, or (ii) are operably coupled to the load inductor and configured to selectively adjust the impedance between the load inductor and the receiver coil;
   a switching circuit comprising a microcontroller operably connected to a plurality of sub-circuits, wherein each of the plurality of sub-circuits engage an associated one of the plurality of capacitors to operably engage or disengage the associated one of the plurality of capacitors;
   wherein each sub-circuit comprises:
      a pair of back to back field effect transistors that connect the associated capacitor to a ground, and a gate driver operatively controlled by the microprocessor and configured to selectively switch the field effect transistors between an open state, and a closed state, each gate driver comprising:
         a resistor connected to gates of the pair of back to back field effect transistors,
         a transistor of the gate driver, and
         a diode connected to the resistor and to the gates of the pair of back to back field effect transistors on one side and connected to the transistor of the gate driver on the other side, wherein the diode is connected to ground when transistor of the gate driver is turned ON;
   and wherein the microcontroller is configured to receive a measured operating parameter of the adaptive impedance matching wireless power transfer system and to use the measured operating parameter to selectively adjust the impedance between the drive inductor and the transmitter coil or selectively adjust the impedance between the load inductor and the receiver coil.

2. The system of claim 1, wherein the drive inductor forms a portion of the first impedance matching network.

3. The system of claim 1, wherein the load inductor comprises a single loop.

4. The system of claim 1, wherein the first impedance matching network comprises a first π-match network.

5. The system of claim 1, wherein the microcontroller is controlled to selectively adjust the impedance to achieve a capacitance that maximizes the forward transmission gain to the transmitter coil.

6. The system of claim 1, wherein the microcontroller exhaustively engages each combination of the plurality of capacitors to produce an optimal power transfer.

7. The system of claim 1, wherein the microcontroller uses the measured operating parameter with a lookup table to selectively adjust the impedance.

8. The system of claim 1, wherein the microcontroller monitors a measured performance parameter of the system and uses the measured performance parameter to selectively adjust the impedance.

9. The system of claim 1, wherein the microcontroller monitors more than one measured operating parameters of the system, and calculates an optimal capacitance based on the measured operating parameters.

10. The system of claim 1, wherein the at least one switchable bank of capacitors comprises at least five capacitors.

11. The system of claim 1, further comprising a second impedance matching network that is operable to selectively adjust the impedance between the receiver coil and the load inductor.

12. The system of claim 11, wherein the load inductor forms a portion of the second impedance matching network.

13. The system of claim 11, wherein the first impedance matching network comprises a first π-match network with variable capacitances and the second impedance matching network comprises a second n-match network with variable capacitances.

14. The system of claim 1, further comprising a rectifier configured to receive alternating current from the load coil, an active impedance matching circuit configured to receive direct current from the rectifier, and a microcontroller configured to monitor the direct current from the rectifier and to control the active impedance matching circuit to selectively harvest power from the rectifier and provide power to a device.

15. The system of claim 14, wherein the active impedance matching circuit comprises a buck converter.

16. The system of claim 15, wherein the microcontroller selectively adjusts the buck converter.

17. The system of claim 1, wherein the first impedance matching network comprises a first π-match network.

18. The system of claim 1, wherein the measured operating parameter comprises an S-parameter or an RMS voltage measured in the system.

\* \* \* \* \*

UNITED STATES PATENT AND TRADEMARK OFFICE
CERTIFICATE OF CORRECTION

PATENT NO. : 11,090,481 B2
APPLICATION NO. : 16/358528
DATED : August 17, 2021
INVENTOR(S) : Smith et al.

Page 1 of 1

It is certified that error appears in the above-identified patent and that said Letters Patent is hereby corrected as shown below:

In the Claims

| Column | Line | |
|--------|------|---|
| 14 | 2 | change "n-match" to -- $\pi$-match -- |

Signed and Sealed this
Fourteenth Day of June, 2022

Katherine Kelly Vidal
*Director of the United States Patent and Trademark Office*